(12) United States Patent
Kashiwazaki

(10) Patent No.: US 8,681,338 B2
(45) Date of Patent: Mar. 25, 2014

(54) DETECTION DEVICE AND DETECTION METHOD FOR INTERMOLECULAR INTERACTION

(75) Inventor: Osamu Kashiwazaki, Hachioji (JP)

(73) Assignee: Konica Minolta Advanced Layers, Inc., Tokyo (JP)

( * ) Notice: Subject to any disclaimer, the term of this patent is extended or adjusted under 35 U.S.C. 154(b) by 0 days.

(21) Appl. No.: 13/812,353

(22) PCT Filed: May 18, 2011

(86) PCT No.: PCT/JP2011/061369
§ 371 (c)(1),
(2), (4) Date: Jan. 25, 2013

(87) PCT Pub. No.: WO2012/014551
PCT Pub. Date: Feb. 2, 2013

(65) Prior Publication Data
US 2013/0122607 A1 May 16, 2013

(30) Foreign Application Priority Data

Jul. 27, 2010 (JP) ................................ 2010-167835

(51) Int. Cl.
*G01N 21/00* (2006.01)
*G01N 21/55* (2006.01)

(52) U.S. Cl.
CPC .................................... *G01N 21/553* (2013.01)
USPC .............................. 356/445; 436/164; 356/73

(58) Field of Classification Search
CPC ..................................................... G01N 21/553
USPC ............................ 356/445–448, 73, 300–334
See application file for complete search history.

(56) References Cited

U.S. PATENT DOCUMENTS

| 7,439,073 | B2 * | 10/2008 | Fujimura et al. | ............... | 436/164 |
| 2002/0011567 | A1 * | 1/2002 | Ozanich | ........................ | 250/326 |
| 2005/0089993 | A1 * | 4/2005 | Boccazzi et al. | ............ | 435/286.2 |
| 2007/0165217 | A1 * | 7/2007 | Johansson et al. | ............ | 356/301 |
| 2008/0108122 | A1 * | 5/2008 | Paul et al. | ...................... | 435/183 |

FOREIGN PATENT DOCUMENTS

FOREIGN PATENT DOCUMENTS

| JP | 63-200026 | 8/1988 |
| JP | 11-83628 | 3/1999 |
| JP | 11-160317 | 6/1999 |
| JP | 2004-132799 | 4/2004 |
| JP | 2005-321349 | 11/2005 |
| JP | 3786073 | 3/2006 |
| JP | 2009-507569 | 2/2009 |

OTHER PUBLICATIONS

International Preliminary Report on Patentability corresponding to PCT Application No. PCT/JP2011/061369 issued Mar. 12, 2013.
Sandström, T. et al., "Visual detection of organic monomolecular films by interference colors", Applied Optics, Feb. 15, 1985, pp. 472-479, vol. 24, No. 4.
English-language International Search Report from the Japanese Patent Office, mailed Aug. 16, 2011, for International Application No. PCT/JP2011/081369.

\* cited by examiner

*Primary Examiner* — Michael P Stafira
(74) *Attorney, Agent, or Firm* — Finnegan, Henderson, Farabow, Garrett & Dunner, L.L.P.

(57) ABSTRACT

In order to improve the detection accuracy of a reflection spectrum, a detection device for intermolecular interaction is provided with a detector (10) which has a ligand (16), a white light source (20) which emits white light, a spectroscope (30) which detects the spectral intensity of received light, a light transmission unit (40) which has a first light transmission path (41) for transmitting the white light from the white light source to the detector, a second light transmission path (42) for transmitting reflected light of the white light from the detector to the spectroscope, and a third light transmission path (43) for transmitting the white light from the white light source to the spectroscope, a switching unit (80) which performs switching between a reflected light receiving state in which the transmission of the reflected light of the white light in the detector to the spectroscope via the first and second light transmission paths is enabled and a white light receiving state in which the transmission of the white light from the white light source to the detector via the third light transmission path is enabled, and a control unit (50) which controls the switching unit and the spectroscope to perform control for detecting the spectral intensities in the white light receiving state and the reflected light receiving state, respectively.

5 Claims, 14 Drawing Sheets

DETECTION DEVICE AND DETECTION METHOD FOR INTERMOLECULAR INTERACTION

TECHNICAL FIELD

The present invention relates to a detection device and a detection method for intermolecular interactions, in particular, to a detection device and a detection method for detecting intermolecular interactions of, for example, biological molecules and organic polymers.

BACKGROUND ART

Labeling of radioactive or fluorescent substances has generally been employed for conventional measurements of bonds or links such as intermolecular interactions between biomolecules, e.g., antigen-antibody reactions and intermolecular interactions between organic polymers. This labeling, however, is time-consuming, and especially labeling of proteins requires complicated procedures and causes denaturation of the proteins in some cases. RIfS (reflectometric interference spectroscopy) making use of a change in interference color of an optical film is known as a current simplified means for directly detecting bonds or links between biomolecules and organic polymers without labeling. The principle of the RIfS is disclosed in Patent Document 1 and Non Patent Document 1, for example.

RIfS will now be briefly described. RIfS employs a detector 100 shown in FIGS. 15A to 15C. With reference to FIG. 15A, the detector 100 includes a substrate 102 and an optical film 104 provided on the substrate 102. When the detector 100 is irradiated with white light, spectral intensities of the incident white light and reflected light are depicted with solid lines 106 and 108, respectively in FIG. 16. By calculating reflectance from spectral intensities of the incident white light and the reflected light thereof, reflectance spectrum 110 depicted with a solid line is obtained as shown in FIG. 17.

With reference to FIG. 15B, ligands 120 are provided on the optical film 104 in order to detect intermolecular interactions. The ligands 120 provided on the optical film 104 modify the optical thickness 112, leading to a change in light path length, and thus a change in interference wave length. This causes the peak shift of spectral intensity distribution of the reflected light. As a result, the reflection spectrum shifts from a solid line 110 to a dotted line 122 in FIG. 17. A sample solution is then poured over the detector 100, so that binding occurs between ligands 120 on the detector 100 and analytes 130 in the sample solution as depicted in FIG. 15C. The binding of the ligands 120 and the analytes 130 further modifies the optical thickness 112, and the reflection spectrum 122 shifts to the reflection spectrum 132 (a dashed line) in FIG. 17. The detection of a variation in bottom wavelength between the reflection spectra 122 and 132 enables intermolecular interactions to be determined.

FIG. 18 illustrates a temporal transition of the variation in the bottom wavelengths. The variation in the bottom wavelength by the ligand 120 can be observed at a time point 140, while the variation in the bottom wavelength by the bonds or links between the ligand 120 and the analyte 130 can be observed at a time point 142.

PRIOR ART DOCUMENTS

Patent Documents

Patent Document 1: Japanese Patent No. 3786073

Non Patent Documents

Non Patent Document 1: Sandstrom et al, APPL. OPT., 24, 472, 1985

DISCLOSURE OF THE INVENTION

Problems to be Solved by the Invention

In general, a conventional device for measuring intermolecular interactions utilizing the RIfS described above includes a spectrometer for detecting reflected light which has an optical path so as to receive the white light reflected from a substrate of a detector from a light source, and thus is not provided with an optical path for receiving direct white light from a light source. Accordingly, the spectral intensity (wavelength distribution) of the initial white light, required as a reference of the estimation of a reflection spectrum from the substrate, is measured in advance during an adjustment step of the device assembly and is stored as data (hereinafter referred to as reference data). At the actual detection of a specimen, the reference data is read out and used for the estimation of the reflection spectrum.

Such a prepared reference data of wavelength distribution characteristics does not allow for the temperature dependence of a light source at the detection of a specimen or a spectrum change in the wavelength distribution of the light source intensity due to over-time deterioration. Consequently, a reflection spectrum estimated through this reference data a disadvantage, i.e., poor accuracy due to the temperature characteristics and the aging deterioration of the light source.

An object of the present invention is to provide an improvement in detection accuracy of intermolecular interactions.

Means for Solving the Problem

According to one aspect of the present invention, there is provided a detection device for an intermolecular interaction which includes a detector having a ligand, a white light source emitting white light, a spectrometer to detect a spectral intensity of received light, a light transmission unit including a first optical transmission path for transmitting the white light from the white light source to the detector, a second optical transmission path for transmitting reflected light of the white light from the detector to the spectrometer and a third optical transmission path for transmitting the white light from the white light source to the spectrometer, a switching unit switching between a reflected light receiving state which allows the reflected light of the white light at the detector to be transmitted to the spectrometer via the first and second optical transmission paths and a white light receiving state which allows the white light from the white light source to be transmitted to the spectrometer via the third optical transmission path, and a controller controlling the switching unit and the spectrometer to detect the spectral intensities in the white light receiving state and in the reflected light receiving state.

Also, the detection device can include a calculation unit to estimate a reflection spectrum through calculation of a reflectance for every predetermined wavelength range on a basis of the spectral intensities of the white light and the reflected light obtained by the control of the controller.

Further, the switching unit of the detection device can be configured to be a shutter mechanism selectively switchable between an optically shielded state of a light transmission via the first optical transmission path and an optically shielded state of a light transmission via the third optical transmission path with a shielding member, the position of the shielding member being movable.

Alternatively, the switching unit of the detection device can be configured to be a liquid crystal filter selectively switchable between an optically shielded state of a light transmission via the first optical transmission path and an optically shielded state of a light transmission via the third optical transmission path.

According to another aspect of the present invention, there is provided a detection method for detecting an intermolecular interaction using a detection device including a detector having a ligand, a white light source emitting white light, a spectrometer detecting spectral intensity of received light, a light transmission unit including a first optical transmission path for transmitting the white light from the white light source to the detector, a second optical transmission path for transmitting reflected light of the white light from the detector to the spectrometer and a third optical transmission path for transmitting the white light from the white light source to the spectrometer, the method including a first detection step of receiving the reflected light of the white light from the detector via the first and the second optical transmission paths and detecting the spectral intensity of the reflected light by the spectrometer, a second detection step of receiving the white light from the white light source via the third optical transmission path either before or after the first detection step and detecting the spectral intensity of the white light by the spectrometer and a calculation step of estimating a reflection spectrum by calculating a reflectance for every predetermined wavelength range on a basis of the spectral intensities of the white light obtained in the first detection step and the reflected light obtained in the second detection step.

Effect of the Invention

According to the present invention, white light can be transmitted from a white light source to a spectrometer via a third optical transmission path of a light transmission unit, thus the reference spectral intensity of the white light can be detected at the same time together with detection of the spectral intensity of the reflection light from a detector. This allows the spectral intensities of both the white light and reflected light to be detected under substantially identical conditions in terms of a change in temperature and aging deterioration of the white light source, resulting in improved measurement accuracy.

In a case that a switching unit of the detection device includes a shutter mechanism provided with an optical shielding member, the shielding member retracts from the optical transmission path in a nonshielding state. Thus, the switching unit does not hinder the light transmission and suitable light transmission can be achieved.

Alternatively, in a case that the switching unit of the detection device includes a liquid crystal filter, any shape of optical shielding region can be formed even though two optical transmission paths has a complicated cross-sectional structure. Thus, suitable switching of the optical transmission paths can be achieved.

Moreover, these two optical transmission paths can be switched even when the two optical transmission paths to be switched are not separated.

EMBODIMENTS FOR CARRYING OUT THE INVENTION (Configuration of Detection Device for Intermolecular Interaction)

Figure 1:
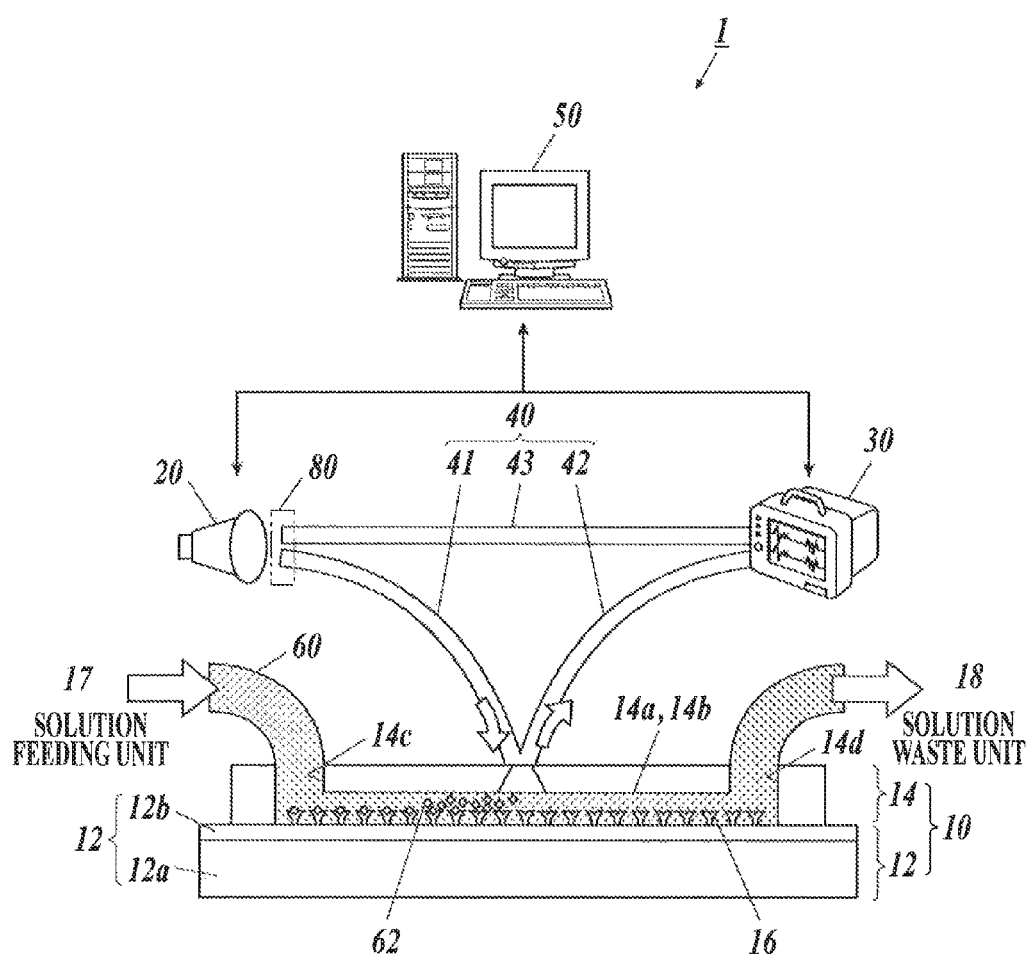
FIG. 1 illustrates an outline configuration of a detection device for intermolecular interactions.
Figure 2A:
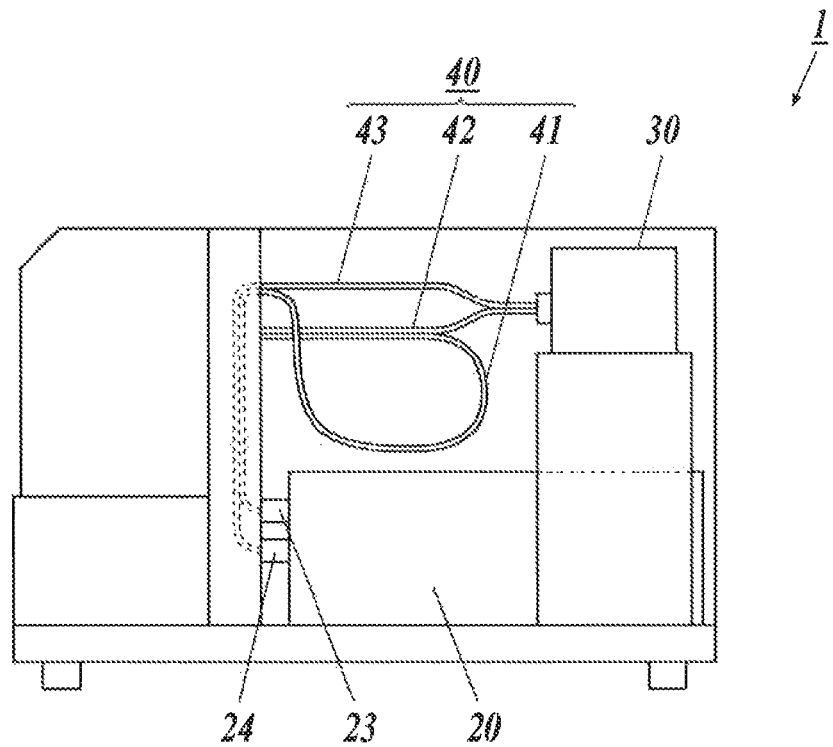
FIG. 2A is a right side view of the detection device, an upper frame and a cover of the device being removed in order for its internal structure to be seen.
Figure 2B:
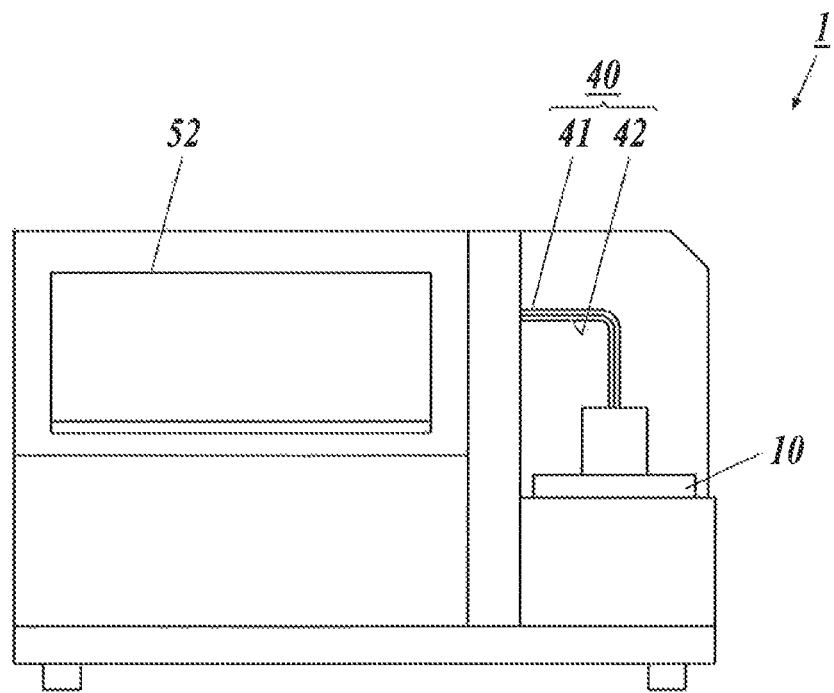
FIG. 2B is a left side view of the detection device, the upper frame and the cover of the device being removed in order for its internal structure to be seen.
Figure 3:
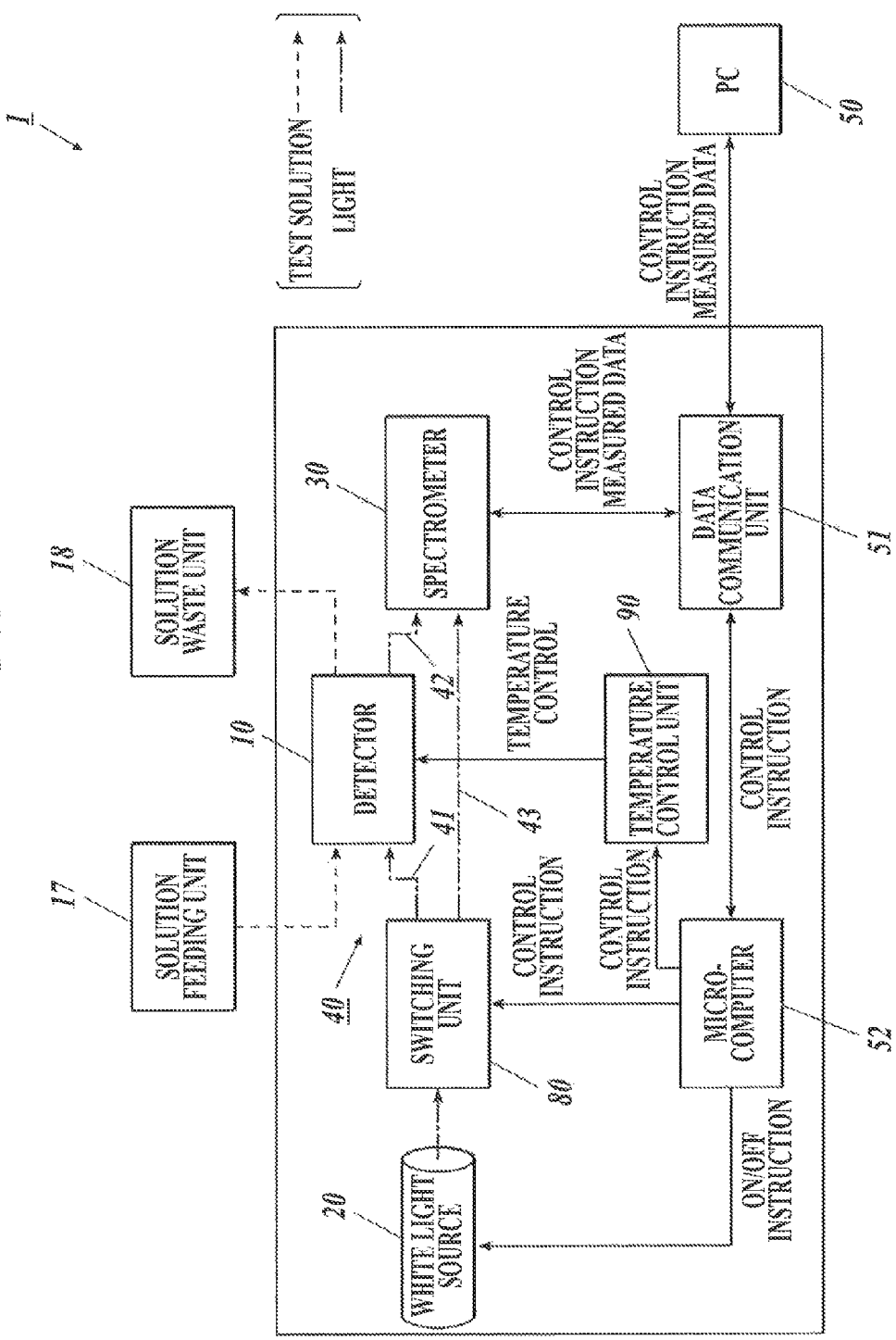
FIG. 3 is a block diagram of the detection device for intermolecular interactions.

Preferred embodiments of the present invention will now be described with reference to the accompanying drawings. FIG. 1 is a schematic view of a configuration of a detection device 1 for intermolecular interaction according to an embodiment of the present invention. FIGS. 2A and 2B are a right side view and a left side view, respectively, of the detection device 1 provided with an upper frame and a cover that are removed in order for the internal structure to be seen. FIG. 3 is a functional block diagram of the detection device 1.

As shown in FIGS. 1 to 3, the detection device 1 mainly includes a detector 10, a white light source 20, a spectrometer 30, a light transmission unit 40, a switching unit 80, a temperature control unit 90, and a controller 50.

The detector 10 basically includes a sensor chip 12 and a flow cell 14.

Figure 4:
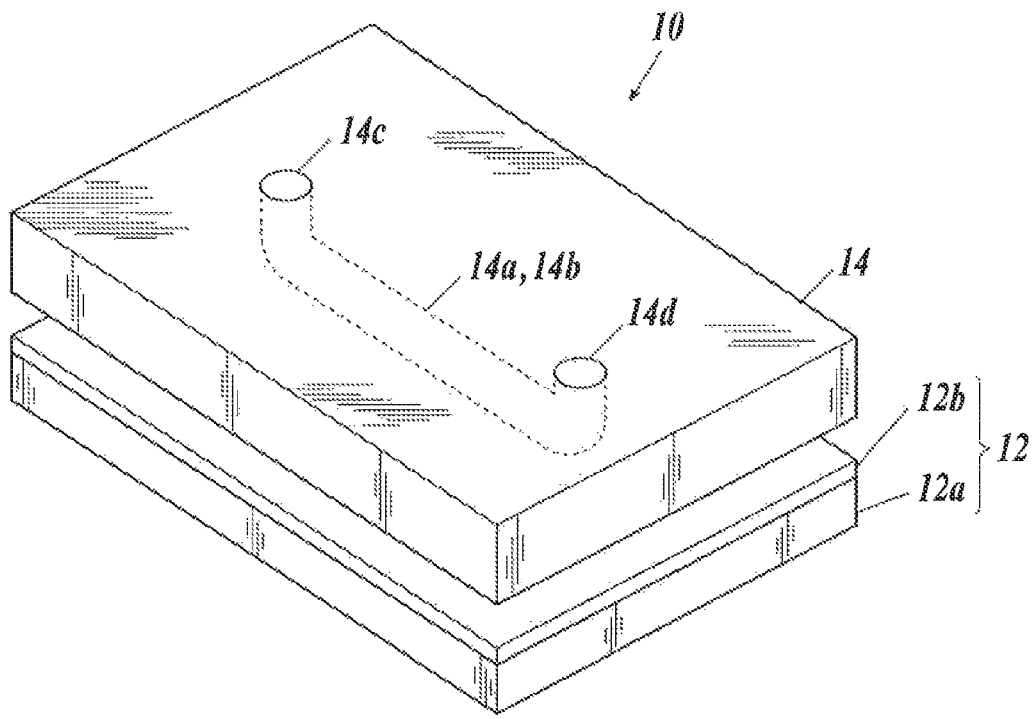
FIG. 4 illustrates an outline configuration of a detector.

FIG. 4 shows that the sensor chip 12 includes a rectangular silicon substrate 12a. A SiN (silicon nitride) film 12b is deposited on the silicon substrate 12a. The SiN film 12b is an exemplary optical thin film.

The flow cell 14 is a transparent member made of silicone rubber. The flow cell 14 has a channel 14a therein. Close contact of the flow cell 14 to the sensor chip 12 defines a closed flow channel 14b (see FIG. 1). Both ends of the channel 14a protrude from the surface of the flow cell 14. One end is connected to a solution feeding unit 17 and serves as an inlet 14c for the supply of a sample solution. The other end is connected to a solution waste unit 18 and serves as an outlet 14d of the sample solution.

Ligands 16 are bound onto the bottom of the channel 14a of the flow cell 14 (see FIG. 1)

In the detector 10, the flow cell 14 is replaceable to the sensor chip 12. This means that the flow cell 14 can be disposable. The surface of the sensor chip 12 can be modified, for example, with a silane coupling agent in order to assist easy replacement of the flow cell 14.

With reference to FIG. 1, end faces of the first optical fiber 41 and the second optical fiber 42, which will be described in detail later, are in close contact with the top surface of the flow cell 14 above the closed flow channel 14b.

The first optical fiber 41 is an optical guide to introduce white light emitted from the white light source 20 to the flow cell 14. When the white light source 20 is turned on, the white light enters the closed flow channel 14b via the first optical fiber 41.

The second optical fiber 42 is an optical guide to introduce the light from the flow cell 14 to the spectrometer 30. This enables the reflected light to be guided to the spectrometer 30 and to be detected when the closed flow channel 14b is illuminated with the white light from the white light source 20.

The temperature control unit 90 includes a temperature control element such as a Peltier element for heating and cooling, and a temperature sensing element. These elements are installed within the detector 10. The controller 50 detects the temperature of the detector 10 by the temperature sensing element through a micro-computer 52 to be described later, and controls the temperature at a predetermined temperature by heating or cooling with the temperature control element.

The light transmission unit 40 includes the first optical fiber 41 as a first optical transmission path to introduce white light from the white light source 20 to the closed flow channel 14b of the flow cell 14, the second optical fiber 42 as a second optical transmission path to introduce the reflected light of the white light from the first optical fiber 41 from the closed flow channel 14b of the flow cell 1 to the spectrometer 30, and the third optical fiber 43 as a third optical transmission path to introduce white light directly to the spectrometer 30 from the white light source 20.

Here, the term "to introduce the white light directly to the spectrometer 30" refers to direct introduction of the white light from the white light source 20 to the spectrometer 30 without any reflection in the midway (other than internal reflection inside the optical fiber).

Each of the optical fibers 41 to 43 described above has a bundled structure of fine fibers.

Figure 5:
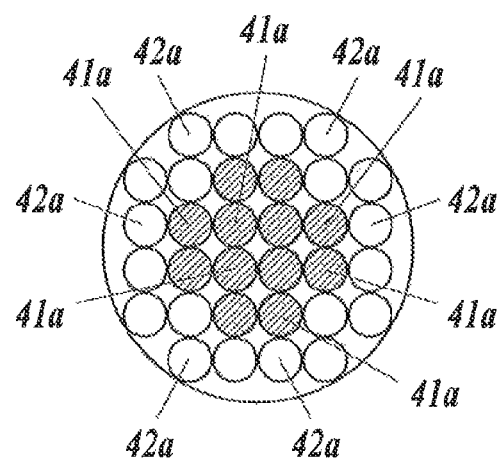
FIG. 5 illustrates an end face of fibers in a detector side at which a first optical fiber and a second optical fiber are combined.

The first optical fiber 41 and the second optical fiber 42 have a common edge on the side of the flow cell 14 at which their fine fibers are compounded into a single bundle as depicted in FIG. 5. More particularly, the fine fibers 41a of the first optical fiber 41 are distributed in the center at the end face on the side of the flow cell 14, and the fine fibers 42a of the second optical fiber 42 are distributed on the periphery as to surround the bundle of the fine fibers of the first optical fiber 41. It should be noted that even though the fine fibers of the first optical fiber 41 are shaded in FIG. 5 for distinguishing of the fine fibers 41a from the fine fibers 42a, both fine fibers 41a and 42a are actually clear and colorless.

Figure 6:
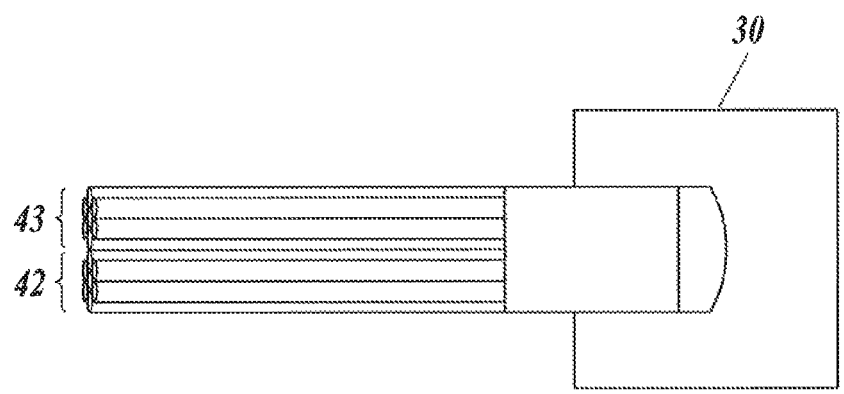
FIG. 6 illustrates an end portion of fibers in a spectrometer side at which a second optical fiber and a third optical fiber are combined.

With reference to FIG. 6, the ends, on the side of the spectrometer 30, of the second optical fiber 42 and the third optical fiber 43 are connected to a connection port for receiving light for the spectrometer 30. Since the spectrometer 30 is equipped with only one connection port, the second optical fiber 42 and the third optical fiber 43 are combined into a single unit at their ends, and the unit is connected to the spectrometer 30.

The spectrometer 30 detects the intensity of the light received by a light receiving unit, for every predetermined wavelength range, and outputs the spectral intensity to the controller 50.

Figure 7:
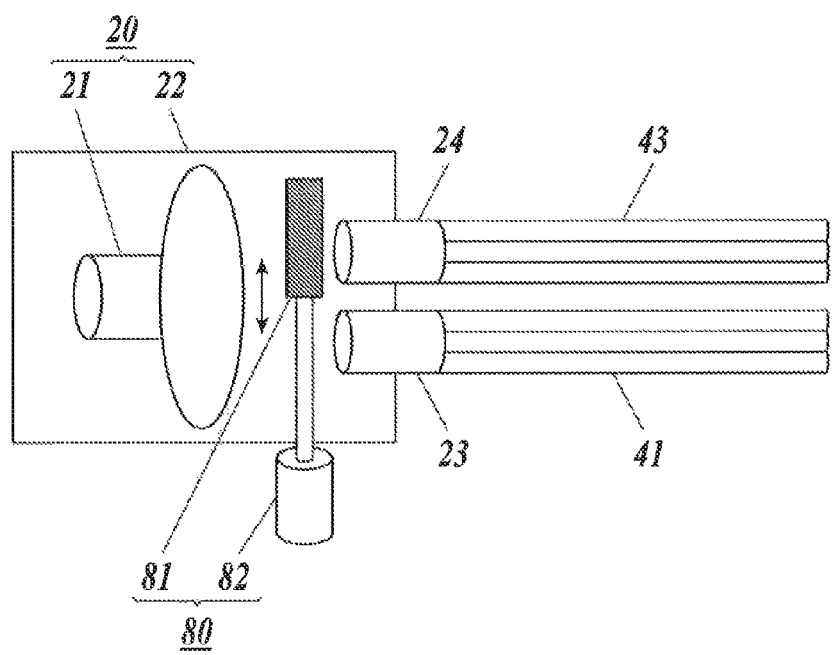
FIG. 7 illustrates a configuration of a white light source and a switching unit.

With reference to FIG. 7, the ends, on the side of the white light source 20, of the first optical fiber 41 and the third optical fiber 43 are connected to two connection ports 23 and 24, respectively, of the white light source 20.

The white light source 20 includes a halogen lamp 21 and a housing 22 to accommodate it. The housing 22 is provided with connection ports 23, 24 for connecting the first optical fiber 41 and the third optical fiber 43, respectively, as described above.

Each of the optical fibers 41 and 43 connected to the connection ports 23 and 24, respectively, has a light incident end face arranged to face the halogen lamp 21, and a switching unit 80 is provided between the halogen lamp 21 and each of the optical fibers 41 and 43.

The switching unit 80 mainly includes a shutter plate 81 functioning as an optical shielding member which can switch between a position to shield the light incident end face of the first optical fiber 41 and a position to shield the light incident end face of the third optical fiber 43, and a stepping motor 82 as a driving source of the shutter plate.

The shutter plate 81 is a flat plate made of a highly light-shielding material, and is sustained by a guide mechanism (not shown) so as to be movable between the two positions mentioned above. Moreover, the shutter plate 81 is provided with a seal to form no gap at the shielded incident end faces of the optical fibers 41 and 43 in order to ensure a high shielding effect.

A conversion mechanism (not shown) from the rotary motion of the stepping motor 82 to a linear motion is also provided between the stepping motor 82 and the shutter plate 81.

It should be noted that the driving source for the switching unit 80 is not limited to the stepping motor 82 and may be any other controllable motor or an actuator such as a linear operating air-cylinder or a solenoid.

The switching unit 80 is controlled through a micro-computer 52 based on the control instructions by the controller 50.

When the incident end face of the third optical fiber 43 is set in the shielded state by the switching unit 80, the closed flow channel 14b of the flow cell 14 is illuminated with white light from the first optical fiber 41, and the reflected light can be transmitted to the spectrometer 30 via the second optical fiber 42 to detect the spectral intensity.

When the switching unit 80 sets the incident end face of the first optical fiber 41 in the shielded state, white light can be transmitted to the spectrometer 30 via the third optical fiber 43, and its spectral intensity can be detected.

The controller 50 includes a PC (Personal Computer), for example, and outputs an execution command for a detection operation control to the detector 10 upon receiving an input to execute the detection operation from an operator. The controller 50 thus functions as a control unit.

The controller 50 also receives the detected data on the spectral intensity of the reference white light from the spectrometer 30 and the observed spectral intensity of the reflected light, and estimates a reflection spectrum through the calculation of reflectance for every predetermined wavelength band. The controller 50 thus functions as a calculation unit.

A data communication unit 51 depicted in FIG. 3 connects the controller 50, the spectrometer 30, and the micro-computer 52, and transmits a control command from the controller 50 to the spectrometer 30 and the micro-computer 52. The data communication unit 51 also sends the spectral intensity data detected by the spectrometer 30 to the controller 50.

The micro-computer 52 executes switching on/off of the white light source 20 in response to a control command from the controller 50, executes the temperature control in the temperature control unit 90 in response to a temperature setting command from the controller 50, and executes the position switching control of the shutter plate 81 in the switching unit 80 in response to a control command from the controller 50.

(Detection Method for Intermolecular Interaction)

Figure 8:
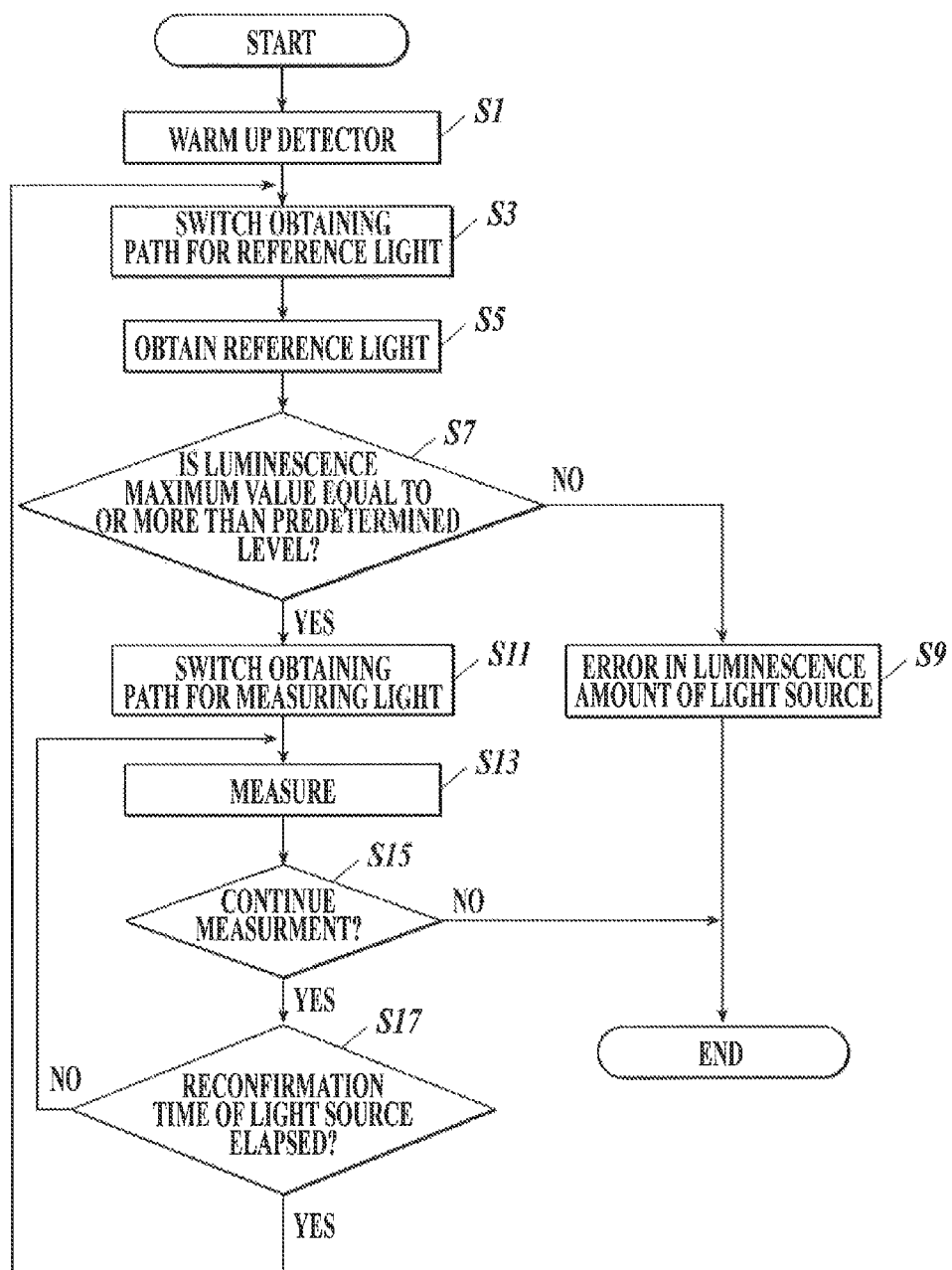
FIG. 8 is a general flow chart illustrating processing steps in a detection method for intermolecular interactions executed by the detection device.

A detection method for intermolecular interaction by the detection device 1 will now be described with reference to FIGS. 8 to 10. FIG. 8 is an operational flow chart of the detection device 1 for detecting a molecular interaction.

The detector 10 is warmed up before the detection starts (Step S1). More specifically, the controller 50 sends the micro-computer 52 a command to hold the temperature at a predetermined temperature, and the micro-computer 52 executes a temperature control through the temperature control unit 90.

After the temperature of the detector 10 is stabilized through the warm-up step, the controller 50 controls the stepping motor 82 of the switching unit 80 through the micro-computer 52 and executes the positional switching control of the shutter plate 81 to shield the incident end face of the first optical fiber 41. This step makes white light of the white light source 20 be introduced to the spectrometer 30 directly, thus ensuring the obtaining path for the reference light through the third optical fiber 43 (Step S3).

The controller 50 then turns on the halogen lamp 21 of the white light source 20 through the micro-computer 52. The spectrometer 30 receives the white light (the reference light) via the third optical fiber 43 to detect the spectrum intensity (Step first detection step).

The controller 50 receives the spectral intensity of the reference light and determines whether or not the maximum optical intensity at a predetermined wavelength band is equal to or more than a predetermined level (Step S7). This is a process to determine whether the optical intensity reduced due to deterioration of the halogen lamp 21. For example, it determines whether the optical intensity reduced to about 90% of that at the beginning of the use.

If the optical intensity is below the predetermined level, the detection process is aborted as an error in luminescence amount of the light source and the process is terminated (Step S9).

If the reference light is no less than the predetermined level, a sample solution 60 including an analyte 62 is supplied from the solution feeding unit 17 to the closed channel 14b of the flow cell 14, and flows through the inlet 14c, the closed channel 14b, and the outlet 14d (see FIG. 1). An analyte 62 is a material which is specifically bound to a ligand 16, and is a target molecule to be detected. Examples of a usable analyte 62 include biomolecules such as proteins, nucleic acids, lipids, and sugars, and foreign substances that are bound to biomolecules, such as drug substances and endocrine-disrupting chemicals.

After the sample solution is supplied to the flow cell 14, the controller 50 controls the stepping motor 82 of the switching unit 80 through the micro-computer 52 and controls the positional switching of the shutter plate 81 to shield the incident end face of the third optical fiber 43. As a result of this operation, white light from the white light source 20 is guided through the first optical fiber 41, and enters to illuminate the closed channel 14b of the flow cell 14. The reflected light at the closed channel 14b is then transmitted to the spectrometer 30 via the second optical fiber 42. An obtaining path to transmit the measuring light is thus ensured through the first and the second optical fibers 41 and 42 (Step S11).

The reflected light (the measuring light) is then received by the spectrometer 30 via the second optical fiber 42, and the spectral intensity is detected (Step S13: second detection step). Then, this spectral intensity is sent to the controller 50.

Next, the controller 50 determines the continuation of the measurement (Step S15). If the measurement is not to be continued, the process terminates. Such a determination may be performed by setting a measuring time to judge whether the measuring time has elapsed, or by setting the measurement to be continued until receiving input of measurement termination to judge the existence or absence of the input of measurement termination.

When the measurement is to be continued, it is determined whether the time period (the reconfirmation time of the light source), after which the spectral intensity of the white light (the reference light) possibly suffers from a change due to the temperature characteristics or the aging deterioration of the light source, has elapsed since the measurement of the spectral intensity of the reference light (Step S17). Here, the reconfirmation time of the light source is preset in the controller 50.

If the reconfirmation time of the light source has not elapsed yet, the process returns to the step S13, and the spectral intensity of the reflected light (the measuring light) is measured again.

If the reconfirmation time of the light source has elapsed already, the process returns to the step S3, and the first optical fiber 41 is switched into the shielded state by the switching unit 80, then the spectral intensity of the white light (the reference light) is detected again.

Thus the controller 50 can acquire the spectral intensity data of the reference light and the spectral intensity data of the measuring light by executing the process control shown in the flow chart of FIG. 8.

The controller 50 calculates the reflectance for every predetermined wavelength band by dividing the observed optical intensity of the measuring light by the measured intensity of the reference light for the same wavelength band and estimates a reflection spectrum, with the spectral intensity of the white light (the reference light) and the spectral intensity of the reflected light (the measuring light).

Figure 9:
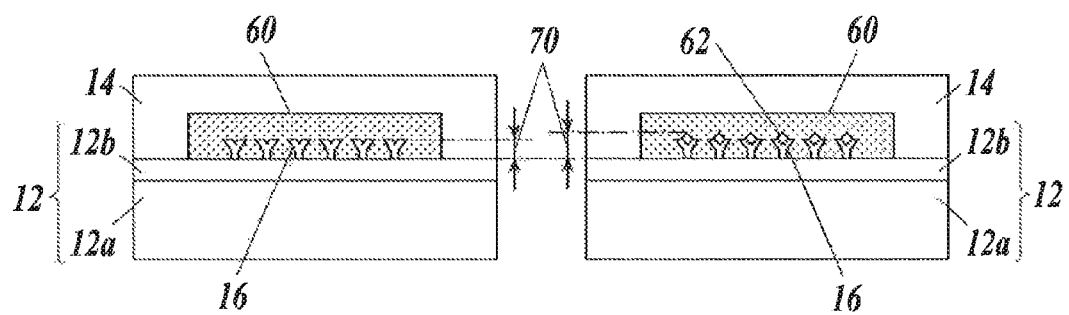
FIG. 9 is a schematic view illustrating binding between a ligand and an analyte.

Once the sample solution is supplied to the closed channel 14b of the flow cell 14, an analyte 62 in the sample solution 60 is bound to a ligand 16 as depicted in FIG. 9. This binding leads to a change in the optical thickness 70, resulting in a modification of the interference color that corresponds to the wavelength of the minimum detected intensity by the spectrometer 30.

The controller 50 calculates and identifies the bottom wavelength $\lambda_{bottom}$ of the reflectance spectrums before and after the binding of the analyte 62 to the ligand 16 from the detection results obtained by the spectrometer 30.

Figure 10A:
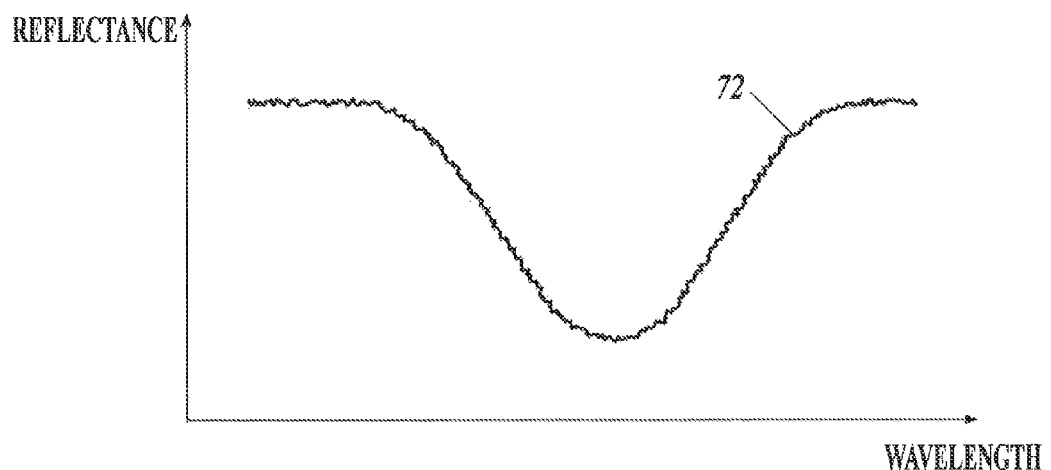
FIG. 10A is a diagrammatic view of a detected reflection spectrum.

The waveform of the reflection spectrum 72 calculated from the spectral intensity data of the reference light and the spectral intensity data of the measuring light obtained by the measurement has an irregular shape with repeated minute asperities which inhibits the calculation and the identification of the bottom wavelength $\lambda_{bottom}$ (see FIG. 10A).

Figure 10B:
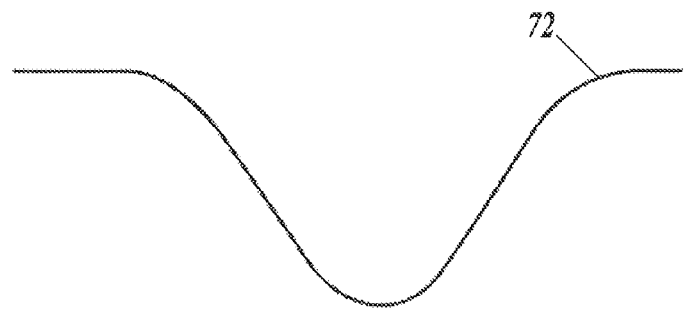
FIG. 10B is a diagrammatic view of a reflection spectrum after approximation by a higher order function.

Accordingly, the wave form of the reflection spectrum 72 is smoothed by approximating the reflection spectrum 72 with a higher order function of approximately 20th order as depicted in FIG. 10B. Such an approximation may use any known method and is achieved, for example, by the sum of a linear function and a pseudo-Voigt function.

The solution (a minimum value) is obtained from such a higher-degree polynomial, and identified as a bottom value.

The controller 50 acquires the spectral intensity data of the reference light and the spectral intensity data of the measuring light periodically through repeated measurements. These measurements result in periodical calculation of the reflection spectrum and estimation of the bottom wavelength $\lambda_{bottom}$ of the reflection spectrum to record its variation over time.

(Advantageous Effects of Embodiment)

As described above, the detection device 1 for a molecular interaction can transmit white light from the white light source 20 to the spectrometer 30 via the third optical fiber 43 of the light transmission unit 40, and thus can detect the reference spectral intensity of the white light at the same time together with the detection of the spectral intensity of the reflection light from the detector 10. As a result, the spectral intensities of both the white light (the reference light) and the reflected light (the measuring light) are detected under substantially identical conditions regardless of the temperature fluctuation and aging deterioration of the white light source 20, and the reflection spectrum can be estimated by the controller 50. Accordingly higher measurement accuracy can be available.

Moreover, the switching unit 80 includes a shutter mechanism and the shutter plate 81 retracts from the incident end face when each of the optical fibers 41 and 43 is not shielded; hence, no attenuating object intervenes in the incident light, ensuring a suitable light transmission.

(Another Example Switching Unit (1))

The location of the switching unit 80 is not limited to the white light source 20. The switching unit can be positioned anywhere if the switching is achieved between a reflected light receiving state and a white light receiving state, the reflected light receiving state being a state where white light is reflected in the detector 10 and can be transmitted to the spectrometer 30 via the first and the second optical fibers 41 and 42 and the white light receiving state being a state where white light can be transmitted from the white light source 20 to the spectrometer 30 via the third optical fiber 43. Consequently the switching unit 80 may be installed either midway along both the first optical fiber 41 and the third optical fiber 43, midway along both the second optical fiber 42 and the third optical fiber 43, or between the second and the third optical fibers 42 and 43 and the spectrometer 30.

Figure 11:
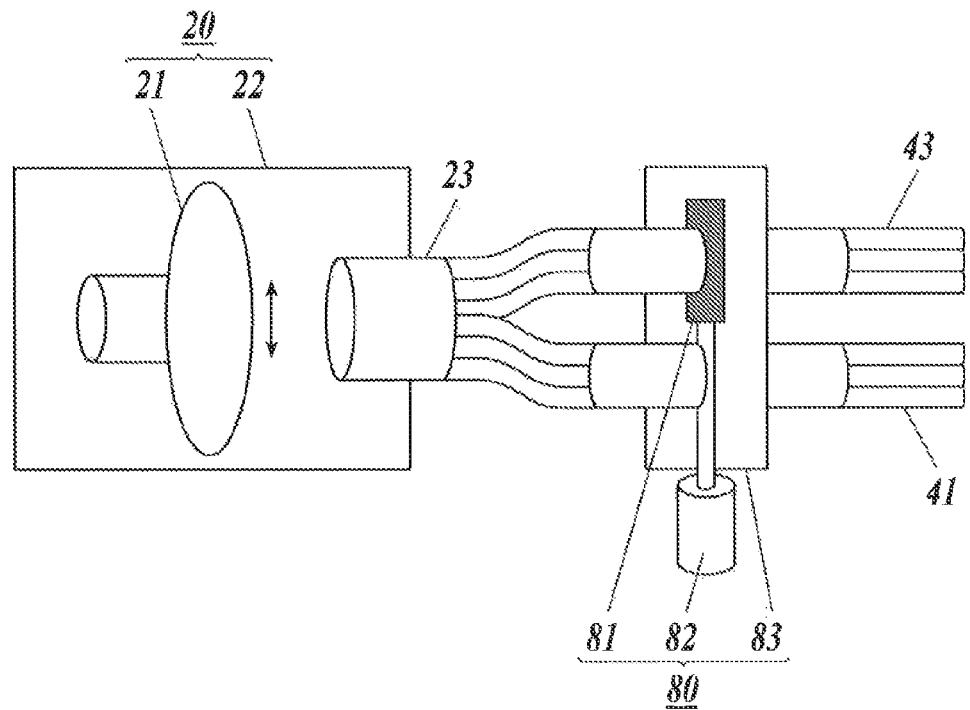
FIG. 11 illustrates an exemplary arrangement of a switching unit installed midway along both the first optical fiber and the third optical fiber.

FIG. 11 illustrates an exemplary arrangement of the switching unit 80 installed midway along both the first optical fiber 41 and the third optical fiber 43. In this case, the shutter plate 81 is disposed in the sectioned first optical fiber 41 and third optical fiber 43. The gaps between the shutter plate 81 and end faces of the respective optical fibers 41 and 43 are sealed in order to avoid light penetration through the gaps.

If the housing 22 of the white light source 20 is equipped with only one connection port 23 in the case that the switching unit 80 is arranged as described above, the first optical fiber 41 and the third optical fiber 43 can be connected to the connection port 23 in a mutually integrated state by combining both ends together. If the switching unit 80 is provided in the middle of an optical fiber in this way, it is preferable to provide a housing 83 in order to prevent penetration of the external light through the gaps at the end faces of respective fibers.

(Another Example Switching Unit (2))

Figure 12:
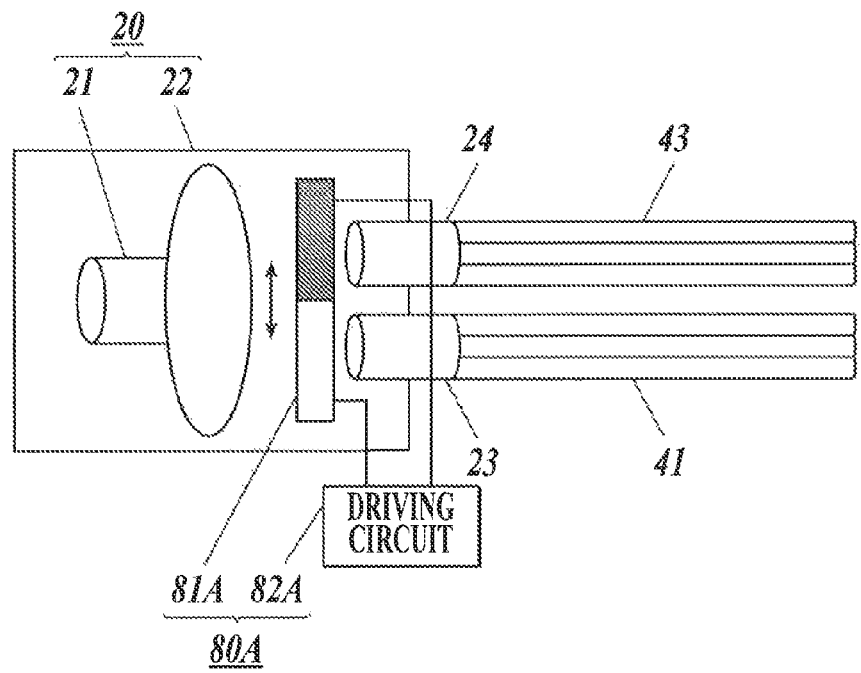
FIG. 12 shows an exemplary arrangement of the switching unit being a liquid crystal filter.

Instead of the switching unit 80 which employs the shutter mechanism, the switching unit 80A which employs a liquid crystal filter 81A is also usable as depicted in FIG. 12.

The switching unit 80A is arranged inside the housing 22 of the white light source 20, and includes the liquid crystal filter 81A in close contact with the incident end faces of the two optical fibers 41 and 43, and its driving circuit 82A. The liquid crystal filter has two shielding areas which cover the incident end face of the first optical fiber 41 and the incident end face of the third optical fiber 43, respectively and which can be switched between a light transmittable state and a shielded state in response to an operational signal from the driving circuit 82A. The driving circuit 82A drives switching of the liquid crystal filter 81A under the control of the micro-computer 52.

Since the liquid crystal filter 81A does not require physical movement of any component, the operation generates little physical gap and high shielding can be achieved. This allows two optical fibers 41 and 43 to be placed closer to each other and the switching unit 80A to be minimized. The switching unit 80A can also be manufactured into any shape to fit an area to be shielded. Even if fine fibers of the optical fibers 41 and 42 are combined into a bundle as in the example shown in FIG. 5, the shielding area can be formed into a shape corresponding to the distribution of respective fine fibers of the optical fibers 41 and 42.

The switching unit 80A using the liquid crystal filter 81A may also be placed either midway along both the first optical fiber 41 and the third optical fiber 43, midway along both the second optical fiber 42 and the third optical fiber 43, or in the position between the second and third optical fibers 42 and 43 and the spectrometer 30.

Figure 13:
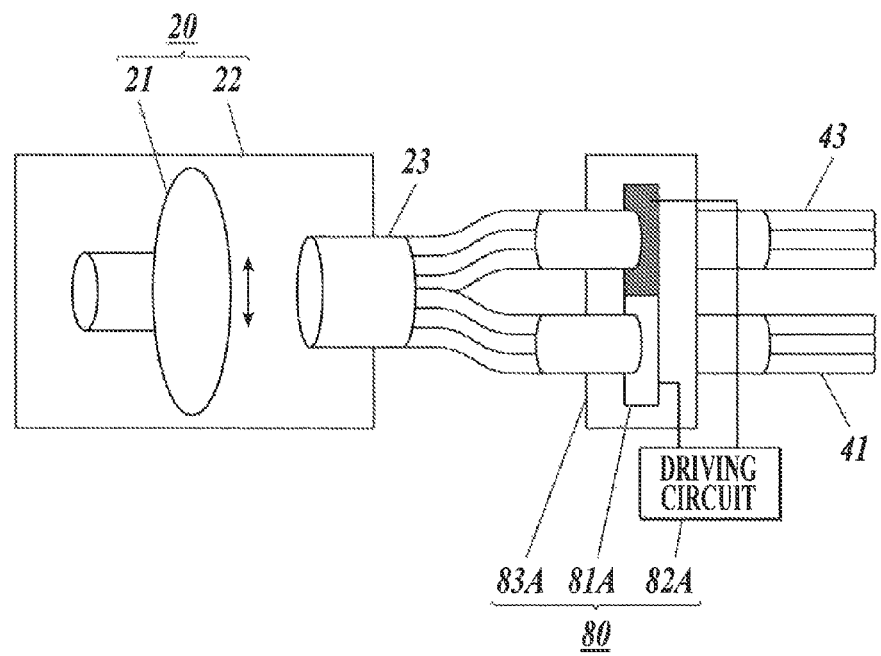
FIG. 13 shows an exemplary arrangement of the switching unit being the liquid crystal filter installed midway along both the first optical fiber and the third optical fiber.

FIG. 13 illustrates an exemplary arrangement of the switching unit 80A installed midway along both the first optical fiber 41 and the third optical fiber 43. In this case, the liquid crystal filter 81A is disposed between split parts of the first optical fiber 41 and between split parts of the third optical fiber 43 as well. The gaps between the liquid crystal filter 81A and each end face of the respective optical fibers 41 and 43 are sealed in order to avoid light penetration through the gaps. Even in this case, it is also preferable to provide a housing 83A in order to prevent penetration of the external light from the gaps at the end faces of respective optical fibers.

(Another Example Connection between Second and Third Optical Fibers and Spectrometer)

In the example depicted in FIG. 6, the second optical fiber 42 and the third optical fiber 43 are combined into a single unit which is connected to the spectrometer 30; however, any other connection can also be employed without restriction.

Figure 14:
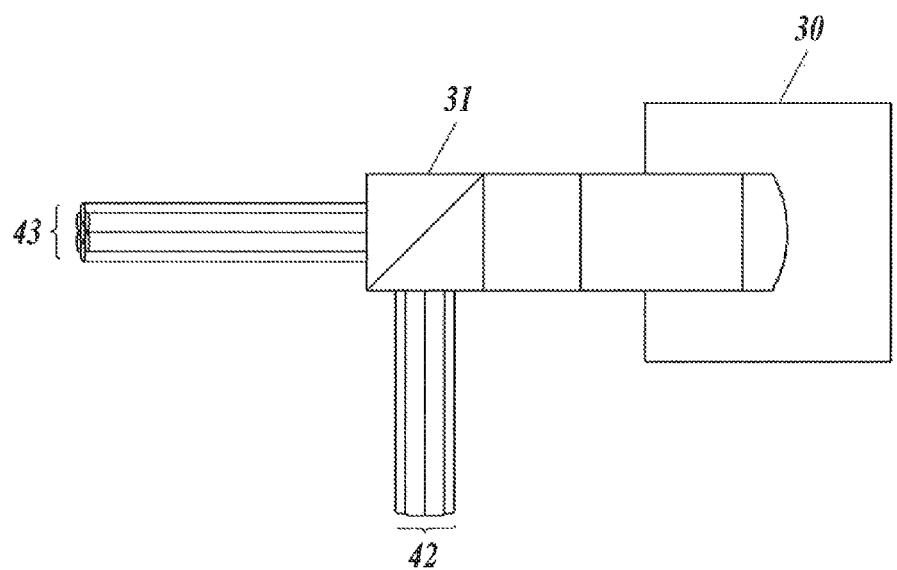
FIG. 14 shows an exemplary connection of the second and third optical fibers to a spectrometer with an optical prism.
Figure 15A:
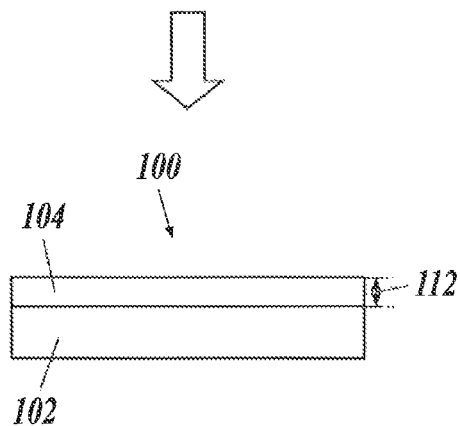
FIG. 15A is one of the sequential drawings explaining the RIfS scheme, illustrating an optical film provided on a substrate.
Figure 15B:
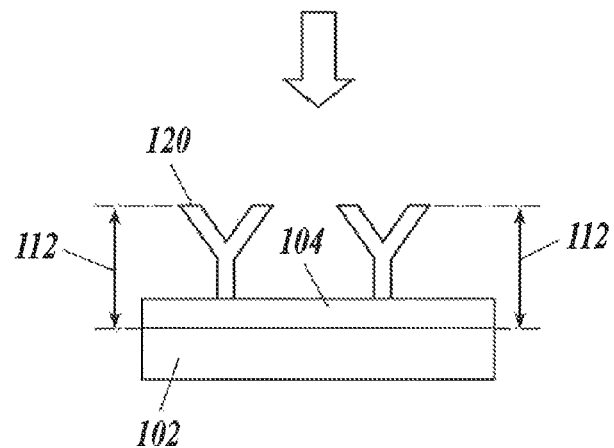
FIG. 15B is one of the sequential drawings explaining the RifS scheme, illustrating a ligand provided on the optical film.
Figure 15C:
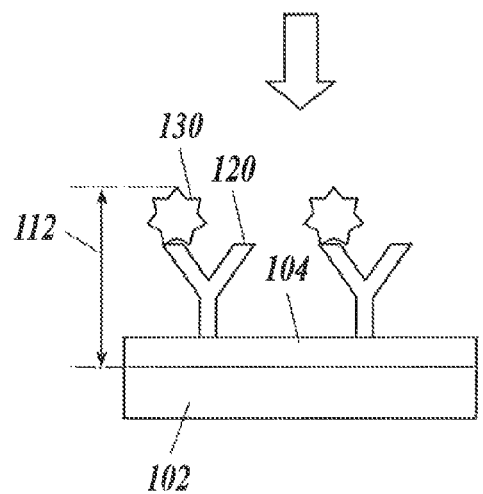
FIG. 15C is one of the sequential drawings explaining the RIfS scheme, illustrating bonding of a ligand and an analyte in a sample solution.
Figure 16:
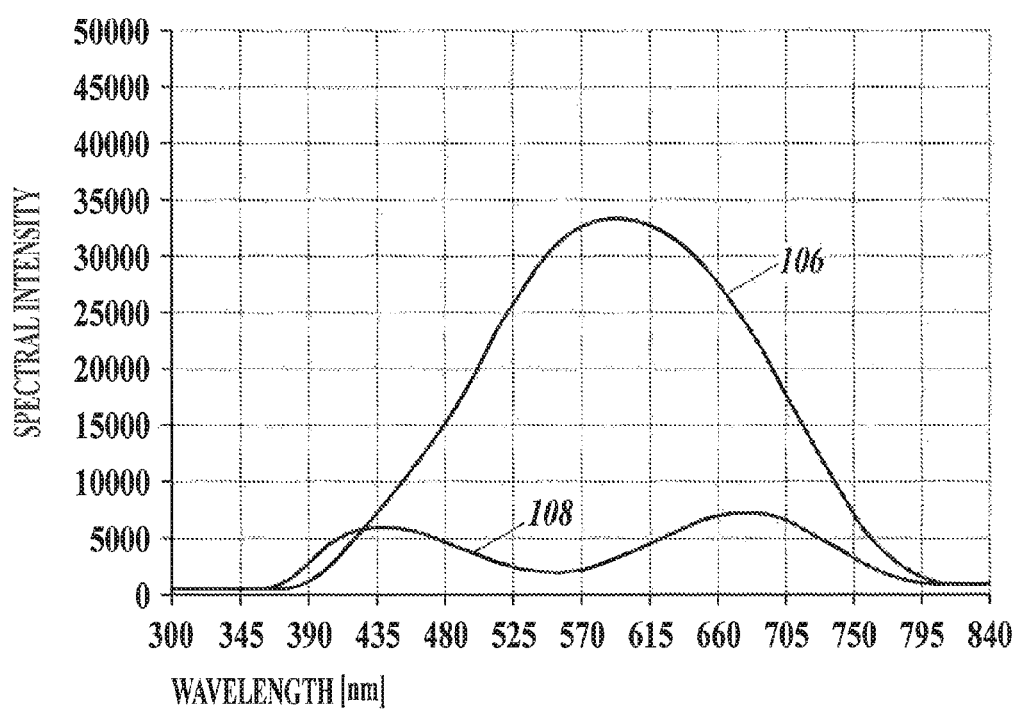
FIG. 16 is an exemplary spectrum exhibiting a general relationship between the wavelength and the spectral intensity.
Figure 17:
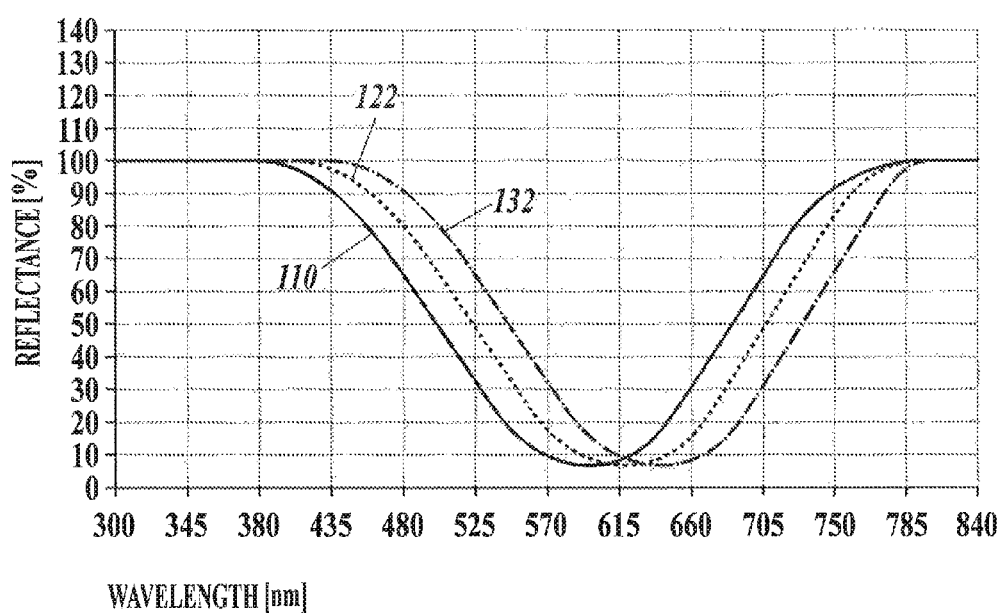
FIG. 17 is an exemplary spectrum exhibiting a general relationship between the wavelength and the reflectance.
Figure 18:
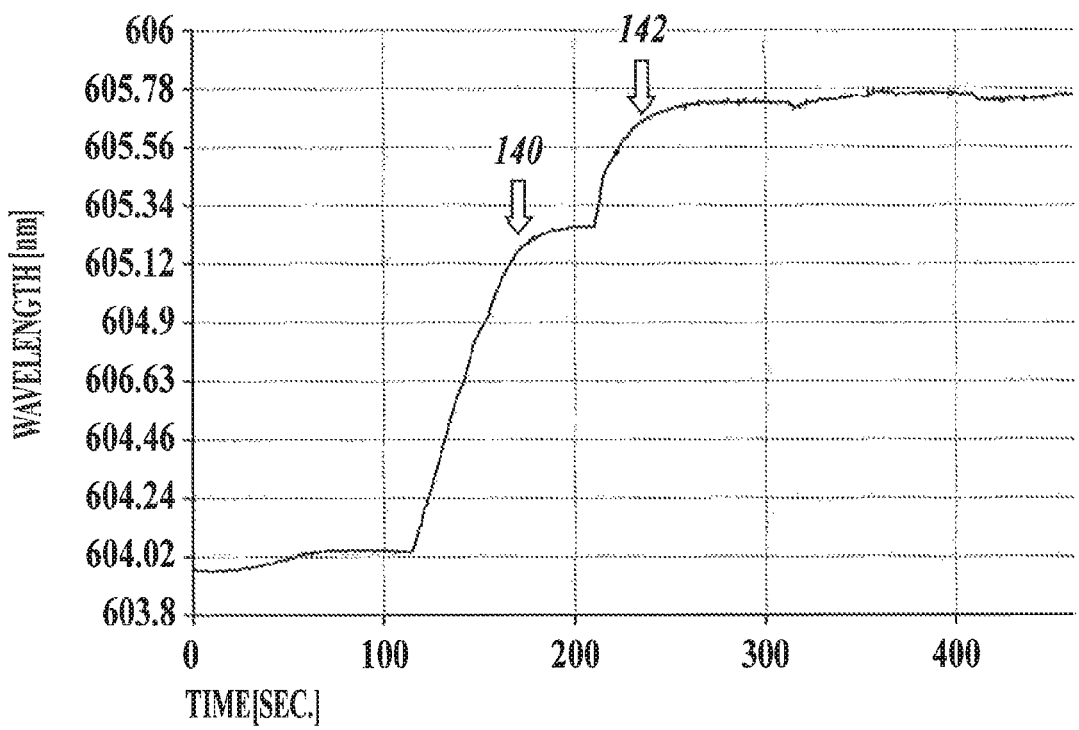
FIG. 18 is a graph illustrating a schematic variation in the bottom wavelength.

For example, a prism 31 which has an internal reflection plane can be used as depicted in FIG. 14. Here two optical fibers 42, 43 are connected in such a manner that the light from one optical fiber 43 for 42) travels straight through the prism to the spectrometer 30, while the light from the other optical fiber 42 (or 43) is reflected at the reflection plane and introduced to the spectrometer 30. In the case of the example in FIG. 6, the spectrometer 30 receives the light from the second optical fiber 42 and the light from the third optical fiber 43 at different areas on a light receiving plane, while in the case of prism utilization, both optical fibers 42 and 43 can introduce light to the same area of the light receiving plane of the spectrometer 30, thus allowing detection condition to be equalized.

Explanation of Reference Numerals
1. detection device
10. detector
12. sensor chip
14. flow cell
16. ligand
20. white light source
30. spectrometer
40. light transmission unit
41. first optical fiber (first optical transmission path)
42. second optical fiber (second optical transmission path)
43. third optical fiber (third optical transmission path)
50. controller
60. sample solution
62. analyte
72. reflection spectrum
80, 80A. switching unit
81. shutter plate (optical shielding member)
81A. liquid crystal filter

The invention claimed is:

1. A detection device for an intermolecular interaction, comprising:
 a detector having a ligand;
 a white light source emitting white light;
 a spectrometer to detect a spectral intensity of received light;
 a light transmission unit including a first optical transmission path for transmitting the white light from the white light source to the detector, a second optical transmission path for transmitting reflected light of the white light from the detector to the spectrometer and a third optical transmission path for transmitting the white light from the white light source to the spectrometer;
 a switching unit switching between a reflected light receiving state which allows the reflected light of the white light at the detector to be transmitted to the spectrometer via the second optical transmission paths and a white light receiving state which allows the white light from the white light source to be transmitted to the spectrometer via the third optical transmission path; and
 a controller controlling the switching unit and the spectrometer to detect the spectral intensities in the white light receiving state and in the reflected light receiving state.

2. The detection device for an intermolecular interaction according to claim 1, further comprising a calculation unit to estimate a reflection spectrum through calculation of a reflectance for every predetermined wavelength range on a basis of the spectral intensities of the white light and the reflected light obtained by the control of the controller.

3. The detection device for an intermolecular interaction according to claim 1, wherein the switching unit is a shutter mechanism selectively switchable between an optically shielded state of a light transmission via the first optical transmission path and an optically shielded state of a light transmission via the third optical transmission path with a shielding member, the position of the shielding member being movable.

4. The detection device for an intermolecular interaction according to claim 1, wherein the switching unit is a liquid crystal filter selectively switchable between an optically shielded state of a light transmission via the first optical transmission path and an optically shielded state of a light transmission via the third optical transmission path.

5. A detection method for detecting an intermolecular interaction using a detection device comprising a detector having a ligand, a white light source emitting white light, a spectrometer detecting spectral intensity of received light, a light transmission unit including a first optical transmission path for transmitting the white light from the white light source to the detector, a second optical transmission path for transmitting reflected light of the white light from the detector to the spectrometer and a third optical transmission path for transmitting the white light from the white light source to the spectrometer, the method comprising:
 a first detection step of receiving the reflected light of the white light from the detector via the first and the second optical transmission paths and detecting the spectral intensity of the reflected light by the spectrometer;
 a second detection step of receiving the white light from the white light source via the third optical transmission path either before or after the first detection step and detecting the spectral intensity of the white light by the spectrometer; and
 a calculation step of estimating a reflection spectrum by calculating a reflectance for every predetermined wavelength range on a basis of the spectral intensities of the white light and the reflected light obtained in the first detection step and the second detection step.

* * * * *